US012746343B2

(12) United States Patent
Boyaval et al.

(10) Patent No.: US 12,746,343 B2

(45) Date of Patent: Sep. 29, 2026

(54) DELIVERY DEVICES FOR ADMINISTERING DRUGS

(71) Applicant: AMGEN INC., Thousand Oaks, CA (US)

(72) Inventors: Margaux Frances Boyaval, Newbury Park, CA (US); Brian Stonecipher, Newbury Park, CA (US); Avon Kuo, San Jose, CA (US); James Chan, San Marino, CA (US); Lisa Nugent, Malibu, CA (US)

(73) Assignee: AMGEN INC., Thousand Oaks, CA (US)

( * ) Notice: Subject to any disclaimer, the term of this patent is extended or adjusted under 35 U.S.C. 154(b) by 921 days.

(21) Appl. No.: 17/256,253

(22) PCT Filed: Jul. 23, 2019

(86) PCT No.: PCT/US2019/042942

§ 371 (c)(1),
(2) Date: Dec. 28, 2020

(87) PCT Pub. No.: WO2020/023451

PCT Pub. Date: Jan. 30, 2020

(65) Prior Publication Data

US 2021/0128844 A1 May 6, 2021

Related U.S. Application Data

(60) Provisional application No. 62/702,641, filed on Jul. 24, 2018.

(51) Int. Cl.

*A61M 5/32* (2006.01)
*A61M 5/31* (2006.01)

(52) U.S. Cl.

CPC ........ *A61M 5/3287* (2013.01); *A61M 5/3135* (2013.01); *A61M 5/326* (2013.01)

(58) Field of Classification Search

CPC ...... A61M 5/3287; A61M 5/20; A61M 5/425; A61M 5/14248; A61M 5/42;

(Continued)

(56) References Cited

U.S. PATENT DOCUMENTS

| | | | |
|---|---|---|---|
| 10,398,854 | B2 | 9/2019 | Fenster et al. |
| 2003/0105430 | A1 | 6/2003 | Lavi et al. |

(Continued)

FOREIGN PATENT DOCUMENTS

| | | | |
|---|---|---|---|
| CN | 101011611 A | 8/2007 |
| CN | 104755119 A | 7/2015 |
| WO | WO-2018081234 A1 | 5/2018 |

OTHER PUBLICATIONS

International Search Report and Written Opinion for International Patent Application No. PCT/US2019/042942, dated Oct. 8, 2019.

(Continued)

*Primary Examiner* — Bhisma Mehta
*Assistant Examiner* — Fatimata Sahra Diop
(74) *Attorney, Agent, or Firm* — MARSHALL, GERSTEIN & BORUN LLP

(57) ABSTRACT

An example drug delivery device includes a syringe assembly including a needle. The drug delivery device includes a handle carrying the syringe assembly and including a first portion, a second portion, a tapered surface, and a window. The first portion being wider than the second portion. The tapered surface extending from the first portion to the second portion. The needle of the syringe assembly adapted to extend from adjacent the second portion during an injection procedure. The window positioned between the first portion and the second portion and adapted to allow contents of the (Continued)

drug delivery device to be viewed. The drug delivery device includes a base adapted to be positioned adjacent the second portion of the handle during at least the injection procedure. The base being wider than the second portion of the handle and adapted to increase stability of the drug delivery device during the injection procedure.

10 Claims, 8 Drawing Sheets

(58) Field of Classification Search
CPC .. A61M 2005/208; A61M 2005/14252; A61M 2005/3139
See application file for complete search history.

(56) References Cited

U.S. PATENT DOCUMENTS

| | | | | |
|---|---|---|---|---|
| 2003/0229308 | A1* | 12/2003 | Tsals | A61M 5/20 604/116 |
| 2014/0296782 | A1* | 10/2014 | Ulrich | A61M 5/158 604/173 |
| 2016/0250470 | A1 | 9/2016 | Malackowski | |
| 2017/0157333 | A1* | 6/2017 | Nguyen | A61M 5/31511 |
| 2017/0239419 | A1* | 8/2017 | McLoughlin | A61M 5/3202 |
| 2017/0357776 | A1* | 12/2017 | Baker | G09B 19/0053 |

OTHER PUBLICATIONS

Chinese Patent Application No. 2019800443513, First Office Action, issued May 27, 2022.

European Patent Application No. 19749154.1, Communication Pursuant to Article 94(3) EPC, dated Nov. 21, 2025.

* cited by examiner

DELIVERY DEVICES FOR ADMINISTERING DRUGS

CROSS-REFERENCE TO RELATED APPLICATION

This is the United States national phase of International Patent Application No. PCT/US19/42942, filed Jul. 23, 2019, which claims priority to U.S. Provisional Patent Application No. 62/702,641, filed Jul. 24, 2018, the entire contents of each of which are hereby incorporated by reference herein.

FIELD OF THE DISCLOSURE

The present disclosure relates generally to delivery devices and, in particular, relates to delivery devices for administering drugs.

BACKGROUND

Drugs can be administered through the use of drug delivery devices such as autoinjectors or on-body injectors. Autoinjectors and on-body injectors may be used to help automate the injection and delivery or administration process, thereby simplifying the process for certain patient groups or sub-groups for which use of the syringe/vial combination or pre-filled syringe systems would be disadvantageous, whether because of physiological or psychological impediments.

Even after receiving specified training in the use of such devices, however, some patients and/or caregivers can experience challenges while using autoinjectors and/or on-body injectors. Such challenges may relate to placement of the device on the person, holding the device during an injection operation and/or removing the device after use.

Specifically, conventional autoinjectors can have an elongate, high-profile housing that requires a user to position and hold the housing through an entire injection operation without additional aid. Conversely, conventional on-body injectors can have a low-profile housing with adhesive extending across a bottom surface thereof so that the housing can be adhered to the skin of the patient for hands-free operation.

SUMMARY

In accordance with a first example, a drug delivery device includes a syringe assembly including a needle. The drug delivery device includes a handle adapted to house at least a portion of the syringe assembly. The handle includes a first portion, a second portion, a tapered surface, and a window. The first portion being wider than the second portion. The tapered surface extending from the first portion to the second portion. The needle of the syringe assembly adapted to extend from adjacent the second portion during an injection procedure. The window positioned between the first portion and the second portion and adapted to allow contents of the drug delivery device to be viewed. The drug delivery device includes a base positioned adjacent the second portion of the handle during at least the injection procedure. The base being wider than the second portion of the handle and adapted to increase stability of the drug delivery device during the injection procedure.

In accordance with a second example, a drug delivery device includes a syringe assembly including a needle and an actuator. The drug delivery device includes a handle carrying the syringe assembly. The handle having a substantially rectangular cross-section and having a height that is less than a width of the handle. The drug delivery device includes a base coupled to the handle and extending outwardly from the handle. The base adapted to be wrapped about a user to secure the drug delivery device during an injection procedure.

In further accordance with the foregoing first and/or second examples, an apparatus may further include any one or more of the following:

In accordance with one example, the base is coupled to the base and includes a flange that extends outwardly from the second portion of the handle.

In accordance with another example, the base includes a suction cup that faces away from the second portion of the handle.

In accordance with another example, the base includes a concave cross-section that faces away from the second portion of the handle.

In accordance with another example, the flange includes a translucent elastomer that is adapted to allow visual access through the flange.

In accordance with another example, the base includes a seal positioned between portions of the flange. The seal being at least one of pierceable by the needle of the syringe assembly during the injection procedure or removable prior to the injection procedure taking place.

In accordance with another example, the handle is removably coupled to the base via a snap-fit connection or a threaded connection.

In accordance with another example, the base includes a cradle comprising a collar and a flange. The collar defining a bore adapted to receive the second portion of the handle during the injection procedure.

In accordance with another example, the collar comprises an interior-tapered surface that defines the bore.

In accordance with another example, the cradle comprises a seal that defines a portion of the bore.

In accordance with another example, the seal is at least one of pierceable by the needle of the syringe assembly during the injection procedure or removable prior to the injection procedure taking place.

In accordance with another example, the second portion of the handle comprises a needle guard.

In accordance with another example, the base is a lid that covers the first portion of the handle prior to the injection procedure.

In accordance with another example, the lid is coupled to the first portion of the handle via a living hinge that is adapted to allow the lid to move approximately 180° from a first position covering the first portion of the handle to a second position. The first portion of the handle and the lid in the second position adapted to increase stability of the drug delivery device during the injection procedure.

In accordance with another example, a rim of the lid includes a low tack adhesive or a non-slip coating.

In accordance with another example, the handle has an oval cross-section.

In accordance with another example, the base includes movable arms that extend from the second portion of the handle. The arms taper outwardly from the second portion of the handle and include portions that are adapted to pinch skin of a user during the injection procedure.

In accordance with another example, the base does not include an adhesive.

In accordance with another example, further including a body including the base. The body defining a cavity that is adapted to removably receive the handle.

In accordance with another example, the body defines an aperture and the syringe assembly includes an actuator adapted to move the needle from a retracted position to an extended position during the injection procedure. The actuator being accessible through the aperture.

In accordance with another example, the base carries at least one fastener. The at least one fastener being adapted to secure the base to the user.

In accordance with another example, the base includes at least one of a hook-and-loop fastener, a clap, or a self-adherent material.

In accordance with another example, the base includes a non-adhesive non-slip coating.

In accordance with another example, the base includes at least one of an arm band or a leg band.

In accordance with another example, the at least one of the arm band or the leg band includes portions carrying at least one fastener to allow the portions of the at least one of the arm band or the leg band to be coupled together.

BRIEF DESCRIPTION OF THE DRAWINGS

The above needs are at least partially met through provision of the examples described in the following detailed description, particularly when studied in conjunction with the drawings, wherein.

DETAILED DESCRIPTION

The examples disclosed herein relate to delivery devices referred to as autoinjectors or hybrid autoinjectors that are structured to fit the lifestyle of a user better than some known and conventional autoinjectors or wearable on-body injectors devices. As such, based on the structure of the disclosed delivery devices, users can choose the interaction they have with the delivery device that is convenient for them. For example, a user can choose to perform an injection procedure using the example delivery devices hands-free by temporarily stabilizing a delivery device to their body or in an assisted manner that may still require some manual holding of the device. Alternatively, a user can choose to rely entirely on a manual holding of the delivery device while the injection procedure is being performed. In some examples, to stabilize the delivery device relative to the body when an injection procedure is being performed, the delivery device includes a stabilizer such as a suction cup, a cradle, adhesive and/or a wrap that is coupled to and/or about the body. Thus, in some examples, the stabilizer is implemented as a fastener that temporarily fastens and/or otherwise stabilizes the delivery device relative to the user.

In examples in which the delivery device is held by the user during an injection procedure, the example delivery devices are structured to be easily held by a user with dexterity or strength challenges to substantially ensure that the injection completes successfully by increasing the grip and/or handle size of the delivery device. Put another way, the form factor of the disclosed delivery devices are structured to be easily held in place against the skin during an injection procedure. Furthermore, because the form factor of the disclosed examples is different than some known delivery devices, users may feel less stigma using the example devices because the delivery devices may be less recognizable as a drug delivery device.

Additionally or alternatively, the example delivery devices are structured to increase a foot print and/or increase the surface area interacting with the skin of the user during an injection procedure to increase stability of the delivery device. As such, the examples disclosed herein enable less adhesive, reduced strength adhesive and/or no adhesive to be used when stabilizing the delivery devices relative to the skin. Reducing and/or eliminating the use of adhesives is especially beneficial for users with thin skin or other skin issues where adhesives may cause negative reactions (e.g., pain, a rash).

Figure 1:
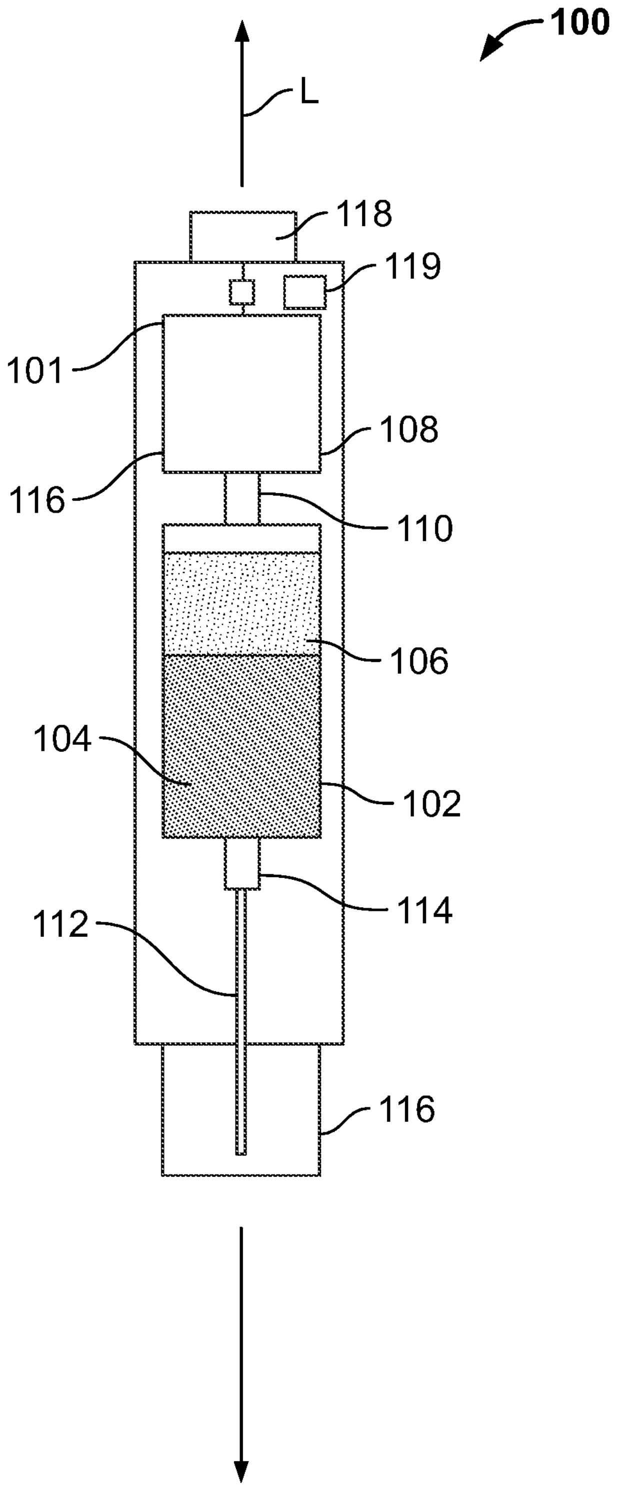
FIG. 1 is a diagrammatic view of an example autoinjector drug delivery device that can be used to implement the disclosed examples.

FIG. 1 illustrates an example delivery device 100, such as autoinjector, having a vertically oriented configuration with some or all drug delivery components disposed in stacked relation along a longitudinal axis L within a housing 101 of the device 100. More specifically, in some examples, the device 100 can be configured to operate and inject a user with the device 100 oriented generally perpendicular to a skin surface of the user. The drug delivery components (e.g., a syringe assembly) can include a reservoir 102 having a drug/therapeutic 104 contained therein, a stopper 106 disposed within the reservoir 102 and sildably movable therein along the longitudinal axis L, a drive mechanism 108 coupled to a plunger 110 to drive the stopper 106 through the reservoir 102, a needle 112 oriented along the longitudinal axis L, a flow path 114 fluidly coupling the reservoir 102 to the needle 112, and a needle insertion mechanism 116 configured to insert the needle 112 to a desired subcutaneous depth within the user. By some approaches, the needle insertion mechanism 116 can be a retractable needle guard to expose the needle 112 or a drive mechanism to longitudinally move the needle a desired distance. For example, the drive mechanism 108 can be configured to drive both movement of the stopper 106 and the needle 112 by moving some or all of the reservoir 102, the flow path 114, and needle 112. As commonly configured, one or more of the components of the device 100, such as the drive mechanism 108 and the needle insertion mechanism 116, can be operable in response to actuation of a user input device 118 accessible on an exterior of the housing 101. Suitable drive mechanisms include, but are not limited to, springs, gas sources, phase changing materials, motors, or other electro-mechanical systems. Pursuant to this, the device 100 can include electronic components, such as a controller 119, to control operation of one or more of the drug delivery components. It will be understood that although FIG. 1 shows the components centered along the longitudinal axis L, one or more of the components can be disposed off center from the longitudinal axis L within the housing 101 and still be considered to be in a stacked relation. In one example, an autoinjector drug delivery device having drug delivery components in a stacked relation corresponds to the reservoir 102 co-axially aligned with the needle 112. Example auto-injector devices are described in U.S. Ser. No. 62/447,174, filed Jan. 17, 2017, which is hereby incorporated by reference herein.

Figure 2:
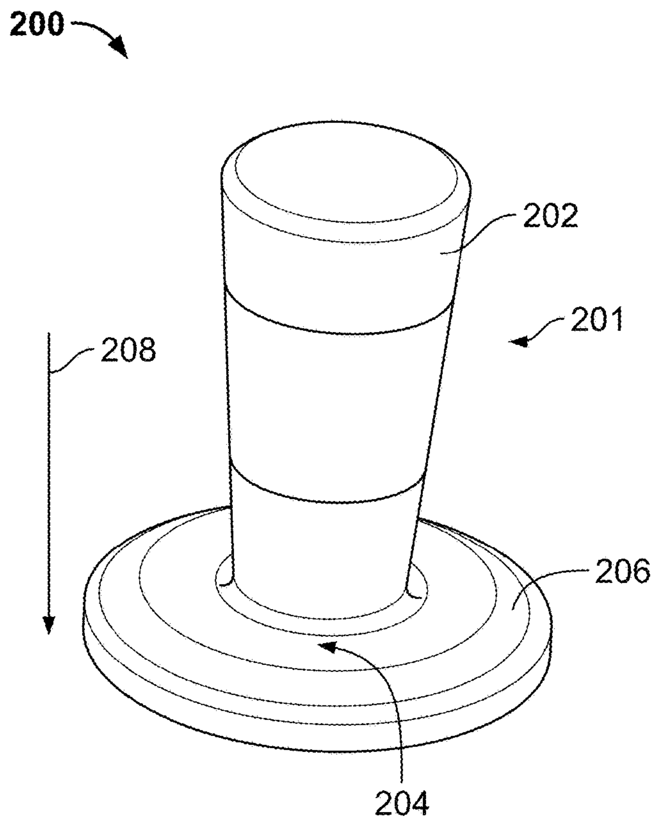
FIG. 2 illustrates an isometric view of an example delivery device in accordance with the teachings of this disclosure.

FIG. 2 illustrates an isometric view of an example delivery device 200 that can be used to administer injections in accordance with the teachings of this disclosure. In the illustrated example, the delivery device 200 includes a body 201 having a non-cylindrical shape and, specifically, is shown having a mushroom-shaped cross-section. As shown, the body 201 includes an example handle 202 and an example base 204 having an example flange 206.

To reduce the likelihood that the delivery device 200 is inadvertently moved when a user is receiving an injection, the flange 206 and/or the base 204 is structured to form a vacuum or suction between the skin of the user and the base 204 when pressure is applied to the delivery device 200 in a direction generally indicated by arrow 208. For example, the base 204 and/or the flange 206 may include a suction cup with a concave cross-section formed of an elastomer, rubber and/or another soft material that bends and/or otherwise conforms to contours of the skin when a force is applied to the handle 202. To enable the user to view the area where the injection is to take place and/or to otherwise provide the user with visual access through the flange 206, in some examples, the base 204 and/or the flange 206 is translucent. While the base 204 including the suction cup is shown carried and/or permanently affixed to the delivery device 200, in other examples, the base 204 is removably coupled to the handle 202 using a fastener such that a user can select whether or not to use the base 204. The fastener may be implemented a snap-fit connection, a threaded connection, etc.

Figure 3:
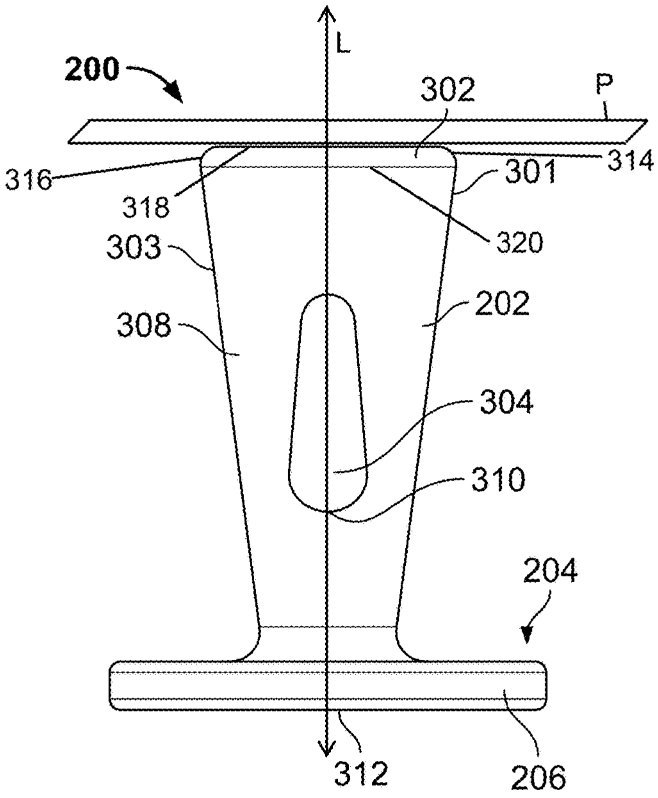
FIG. 3 illustrates a side view of the delivery device of FIG. 2.

FIG. 3 illustrates a side view of the example delivery device 200 of FIG. 2. As shown, an end 301 of the handle 202 includes and/or carries an example actuator 302 that is pressable to cause an internal mechanism to effectuate needle insertion into the patient and subsequent drug delivery such that a user of the device 200 receives an injection. While the actuator 302 can be implemented in different ways, in this example, the actuator 302 is implemented as a button such as, for example, the user input device 118. As also shown, an exterior surface 303 of the handle 202 tapers toward the base 204 and includes an example window 304 that enables contents of the delivery device 200 to be viewed. An upper surface 314 includes a topmost surface 316 positioned within a plane P that is perpendicular to the longitudinal axis L and a corner surface 318. The corner surface 318 is connected to the topmost surface 316 and terminates at an exterior edge 320 immediately upon bending to be perpendicular to the plane. In some examples, the viewable contents includes liquid housed in the reservoir 102. To provide a relatively smooth transition between the window 304 and a surrounding surface 308 of the handle 202, an example chamfered surface 310 is shown positioned between the window 304 and the surrounding surface 308. To deter contaminants and/or debris from accessing the drug delivery components (see FIG. 1) of the delivery device 200 in transit, for example, in this example, a bottom surface 312 of the base 204 forms a seal that is piercable by the example needle 112 of the drug delivery components (see FIG. 1) during an injection procedure. In other examples and to deter occlusion of the needle 112 from occurring, for example, a removable liner covers an aperture defined by the bottom surface 312 through which the needle 112 is to extend. In such examples, the liner is removed prior to the injection procedure taking place.

Figure 4:
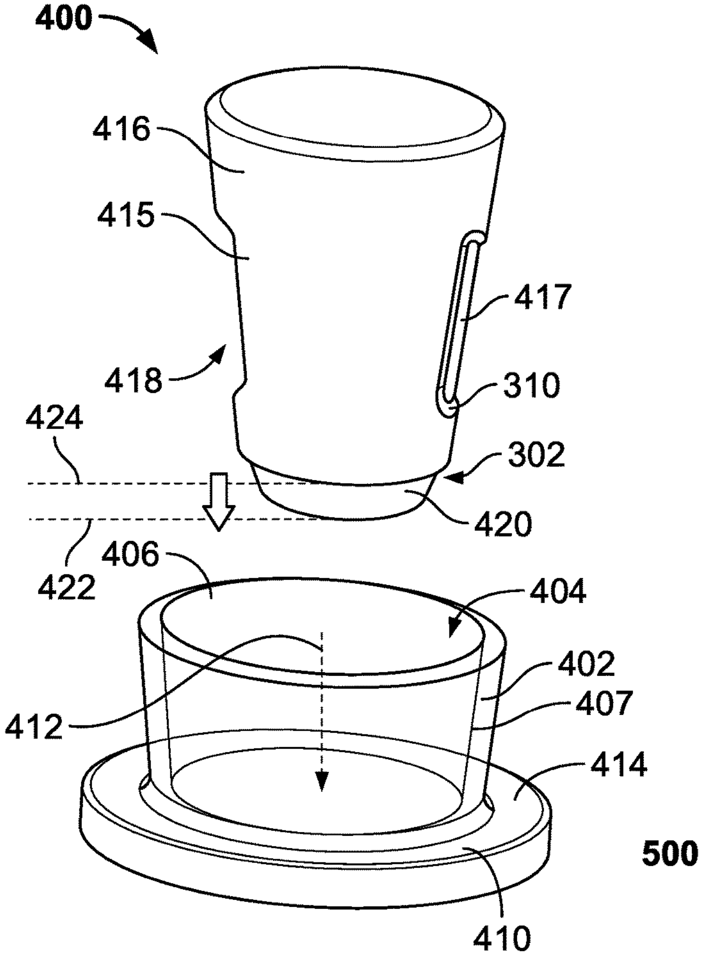
FIG. 4 illustrates an isometric view of another example delivery device structured to be received in an example cradle.

FIG. 4 illustrates an isometric view of another example delivery device 400 that can be used to administer injections in accordance with the teachings of this disclosure. In contrast to the delivery device 200 disclosed in connection with FIG. 2, the delivery device 400 of FIG. 4 includes a base that defines a cradle 402. As shown, the cradle 402 includes a bore/an aperture 404 defined by a tapered surface 406 of a collar 407 that is structured to guide the delivery device 400 toward a bottom wall 410 of the cradle 402 during an injection procedure. As also shown, the cradle 402 includes the bottom wall 410 having an example seal 412 and an example flange 414. In this example, the seal 412 is structured to be piercable by the needle 112 of the drug delivery components (see FIG. 1) when an injection procedure is taking place and the flange 414 is structured to be loosely held against the skin by the user. In other examples, the cradle 402 does not include an adhesive and does not include a seal. In some such examples, the cradle 402 is formed of a tackier material that deters the cradle 402 from moving during an injection procedure. Alternatively, the seal 412 can be implemented as a removable liner that covers an aperture defined by the bottom wall 410 through which the needle 112 is to extend. In such examples, the seal 412 is removed prior to the injection procedure taking place.

In some examples, the flange 414 deters the cradle 402 and/or the delivery device 400 from tipping when the injection procedure is taking place. The cradle 402 may be made of any suitable material such as, for example, a translucent material that enables visual access through the cradle 402. Additionally or alternatively, in some examples, the bottom wall 410 of the cradle 402 is structured to form a vacuum and/or suction when the bottom wall 410 is pressed against skin of a user to deter the delivery device 400 from moving when an injection is being administered. Additionally or alternatively, in some examples, the bottom wall 410 of the cradle 402 includes a low-tack adhesive and/or a non-slip coating to assist in positioning the cradle relative to the skin during an injection procedure and/or to deter the delivery device 400 from moving when an injection is being administered.

In the illustrated example, the delivery device 400 includes a body 415 having a non-cylindrical shape. As shown, the body 415 includes an example handle 416 having first and second windows 417, 418 and an example needle guard 420. In this example, the needle guard 420 is movable from a first and/or extended position generally represented by line 422 and a second and/or retracted position generally represented by line 424. In some examples, the needle guard 420 triggers and/or implements the actuator 302 initiating an injection procedure, for example. In some examples, the delivery device 400 includes a spring that biases the needle guard 420 toward the extended position.

Figure 5:
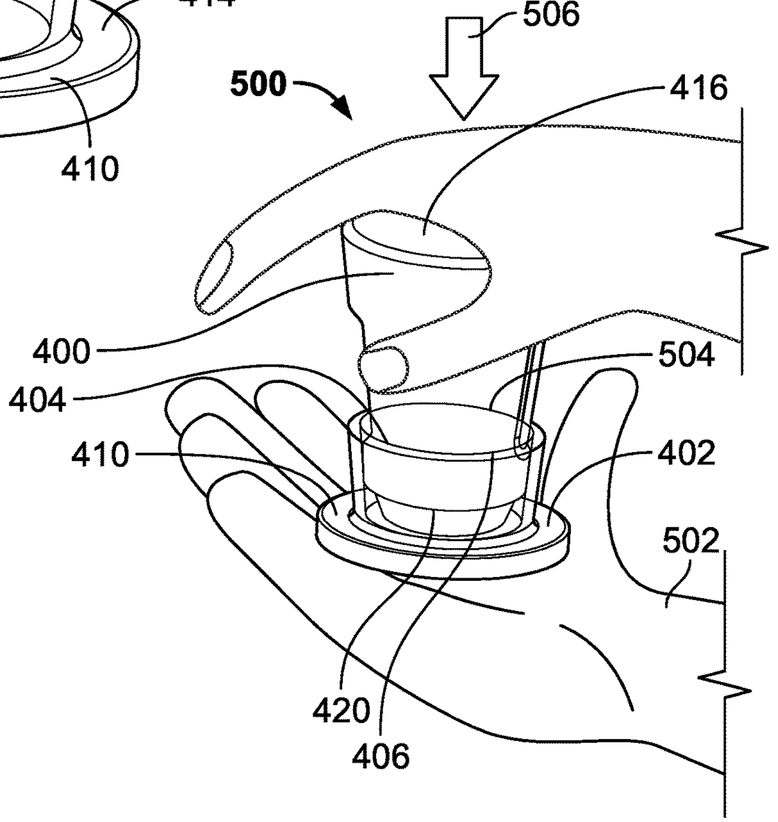
FIG. 5 illustrates the example delivery device and cradle of FIG. 4 being used during an injection procedure.

As shown in FIG. 5, to administer an injection, a user 500 places the cradle 402 adjacent their skin 502 and guides the delivery device 400 into the aperture 404 and toward the bottom wall 410 of the cradle 402. To assist in guiding the delivery device 400 toward a pre-injection position, in the illustrated example, a contour and/or taper of an exterior surface 504 of the delivery device 400 corresponds to the tapered surface 406 that defines the aperture 404. To deploy the needle 112, the user 500 moves the delivery device 400 within the cradle 402 in a direction generally indicated by arrow 506 to retract the needle guard 420, to enable the needle 112 to pierce the seal 412 of the bottom wall 410 (if the seal 412 was not previously removed) and for the injection to be administered. To retain the needle guard 420 in the retracted position during an injection procedure, in some examples, the needle guard 420 and interior surfaces of the handle 416 are sized to engage and/or form an interference fit.

Figure 6:
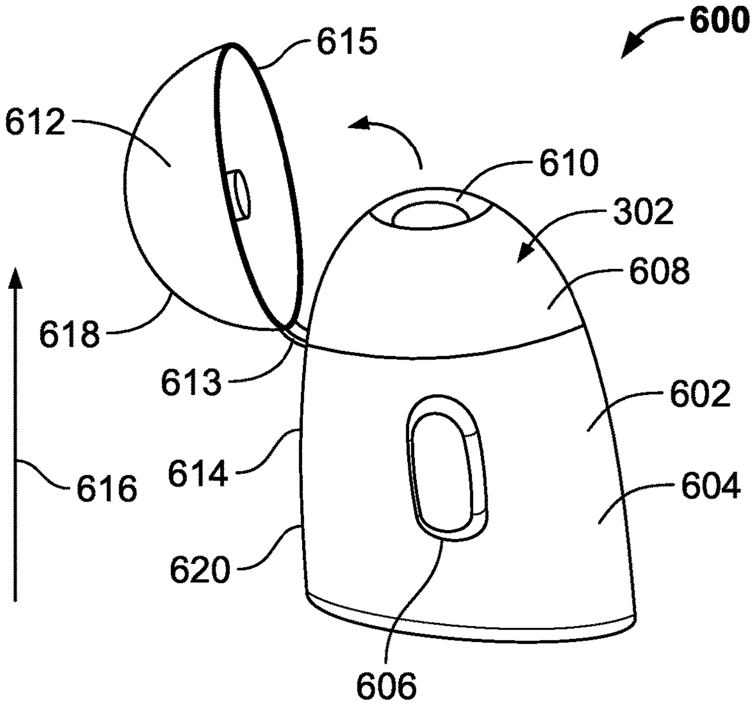
FIG. 6 illustrates an isometric view of another example delivery device including an example support structured to provide increased stability during an injection procedure.

FIG. 6 illustrates a side view of yet another example delivery device 600 that can be used to administer injections in accordance with the teachings of this disclosure. In the illustrated example, the delivery device 600 includes a body 602 having a non-cylindrical shape. In this example, the body 602 includes an example handle 604 defining an example window 606 and an example needle guard 608 carried at an end 610 of the delivery device 600. As shown, the body 602 has a conical shape with an oval cross-section and the needle guard 608 has an arc-shaped side profile.

To increase the stability of the body 602 when the user is receiving an injection and/or to enable a relative angle between the body 602 and the user to be achieved, in this example, the body 602 includes an example support/base 612. As shown, the support 612 is coupled to the body 602 by a living hinge 613 adjacent a first side 614 of the body 602. While the support 612 is shown coupled to the body 602 by the living hinge 613, in other examples, the support 612 may be coupled to the body 602 in any other way that increases stability of the delivery device 600 during an injection procedure. For example, the support 612 can be coupled to the body 602 using a snap connection such that a surface and/or a rim 615 of the support 612 faces a direction generally indicated by arrow 616. In some examples, the rim 615 of the support 612 includes a low tack adhesive or a non-slip coating to further deter movement of the delivery device 600 during the injection procedure.

In this example, the support 612 is implemented by a lid that is structured to cover the end 610 of the delivery device 600 prior to use and to be positioned approximately 180° relative to the body 602 when an injection procedure takes place. As shown, exterior surfaces 618, 620 of the support 612 and the body 602 have contours that correspond and/or the living hinge 613 is dimensioned such that when the end 610 of the delivery device 600 engages the skin of a user, the exterior surfaces 618, 620 and/or the living hinge 613 interact to enable a threshold angle between the delivery device and the skin to be satisfied. In some examples, the threshold angle is approximately 90°. However, the threshold angle may be any other angle.

Figure 7:
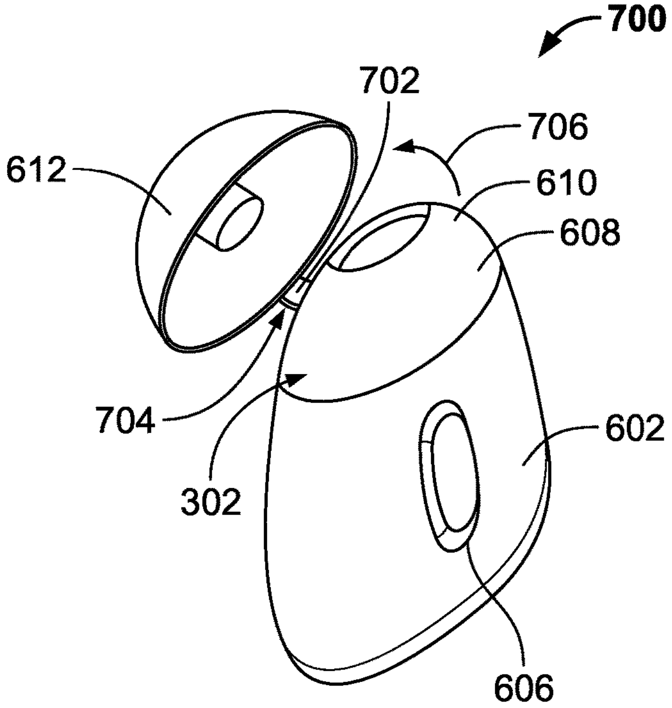
FIG. 7 illustrates an isometric view of another example delivery device that is similar to the delivery device of FIG. 6, except that the support of the delivery device of FIG. 7 is coupled to the body of the delivery device of FIG. 7 in a different location.

FIG. 7 illustrates an example delivery device 700 that is similar to the delivery device 600 of FIG. 6. In contrast to the delivery device 600 of FIG. 6, the support 612 is coupled to the delivery device 700 of FIG. 7 via an example living hinge 702 at a second side 704 of the body 602 different from the first side 614 of the body 602.

Figure 8:
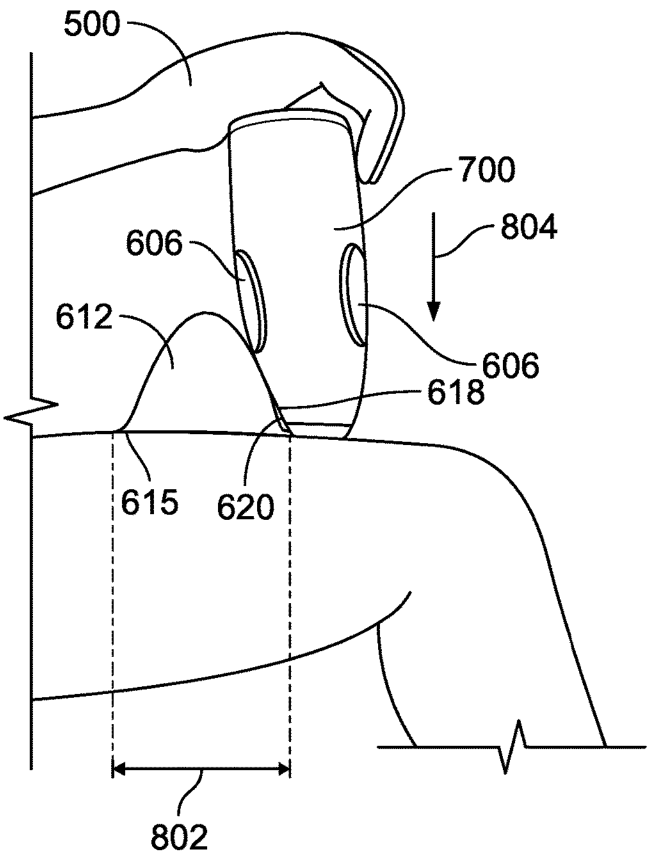
FIG. 8 illustrates the example delivery device of FIG. 7 being used during an injection procedure.

As shown in FIG. 8, to administer an injection, the user 500 moves the support 612 from covering the end 610 of the body 602 in a direction generally represented by arrow 706 (FIG. 7) to enable the corresponding exterior surfaces 618, 620 to interact and to provide a larger effective surface area 802 to stabilize the delivery device 700 on the user 500. To deploy the needle 112, the user 500 moves the delivery device 700 in a direction generally indicated by arrow 804 to retract the needle guard 608 and to enable the needle 112 to administer the injection.

Figure 9:
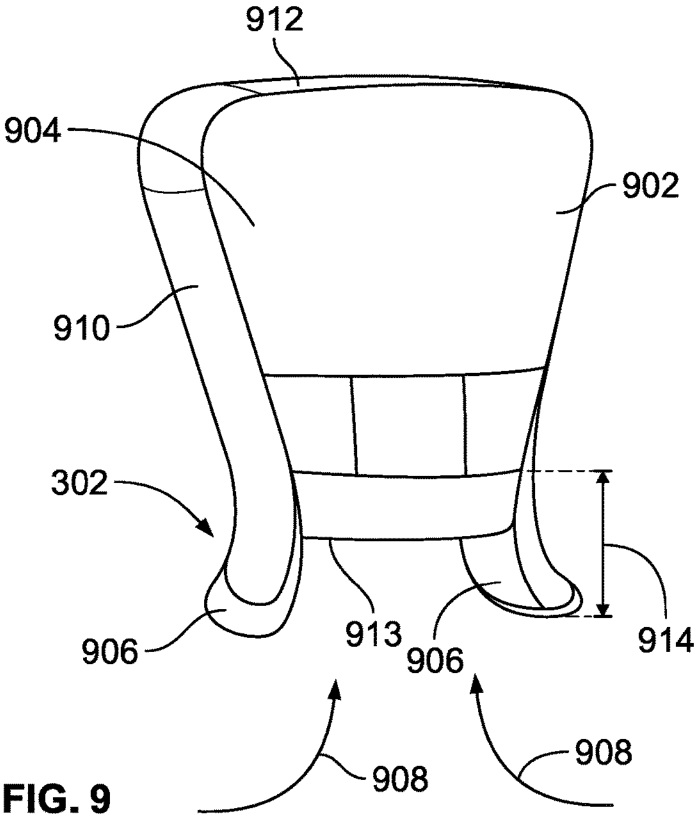
FIG. 9 illustrates another example delivery device that can be used to implement the teachings of this disclosure, where the delivery device of FIG. 9 includes example movable arms structured to pinch skin adjacent an injection area during an injection procedure.

FIG. 9 illustrates an isometric view of still another example delivery device 900 that can be used to administer injections in accordance with the teachings of this disclosure. In the illustrated example, the delivery device 900 includes a body 902 having a non-cylindrical shape. In this example, the body 902 includes an example handle 904 and a base having movable arms 906 that are structured to move in a direction generally indicated by arrows 908 to pinch the skin prior to the user receiving an injection. As shown, the handle 904 includes an exterior surface 910 that inwardly tapers from a second end 912 of the handle 904 toward a delivery end 913 of the body 902. To enable the skin to be pinched by the movable arms 906, the arms 906 extend past the delivery end 913 of the delivery device 900 a distance 914. In this example, the movable arms 906 are implemented as flexible, resilient and/or deformable tabs and/or extensions. To further encourage the arms 906 to pinch the skin, in some examples, the ends are arc-shaped and/or have low tack adhesive or a non-slip coating to enhance position retention. Additionally, in some examples, the movable arms 906 implement the actuator 302 that cause a user of the delivery device 900 to receive an injection after the arms 906 are moved a threshold amount.

Figure 10:
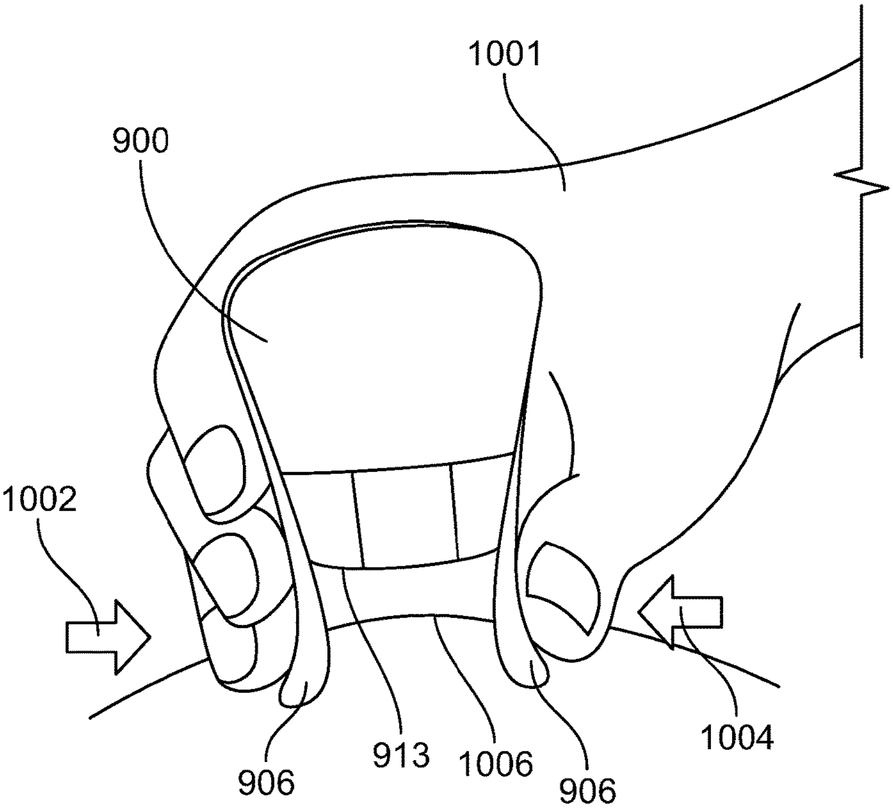
FIG. 10 illustrates the example delivery device of FIG. 9 being used during an injection procedure.

As shown in FIG. 10, to administer an injection, a user 1001 moves the moveable arms 906 inwardly in a direction generally represented by arrows 1002, 1004, by squeezing or pinching to enable the movable arms 906 to pinch skin 1006 directly below the delivery end 913. In some examples, actuating the arms 906 deploys and/or exposes the needle 112 and/or initiates an injection procedure.

Figure 11:
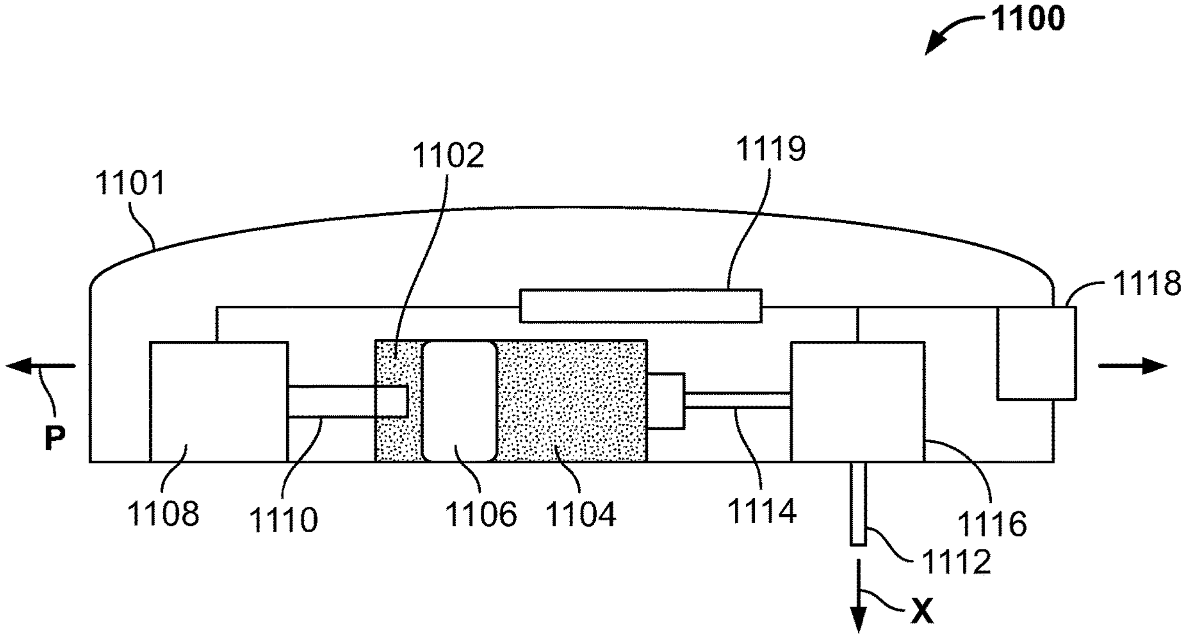
FIG. 11 is a diagrammatic view of an example on-body injector drug delivery device that can be used to implement the disclosed examples.

FIG. 11 illustrates an example delivery device 1100, such as on-body injectors, that can have a horizontally oriented configuration with drug delivery components disposed generally along a horizontal plane P within a housing 1101 of the devices 1100. With the device 1100 illustrated in FIG. 11, the housing 1101 has a low profile with a larger width than height so that when a user positions the housing 1101 on the skin, the components are spread out over an area of the skin rather than stacked as with the above examples. The drug delivery components can include a reservoir 1102 having a drug 1104 contained therein, a stopper 1106 disposed within the reservoir 1102 and sildably movable therein along the horizontal plane P, a drive mechanism 1108 coupled to a plunger 1110 to drive the stopper 1106 through the reservoir 1102, a needle 1112 oriented along an axis X that extends generally perpendicular to the horizontal plane P, a flow path 1114 fluidly coupling the reservoir 1102 to the needle 1112, and a needle insertion mechanism 1116 configured to insert the needle 1112 to a desired subcutaneous depth within the user. As commonly configured, one or more of the components of the device 1100, such as the drive mechanism 1108 and the needle insertion mechanism 1116, can be operable in response to actuation of a user input device 1118 accessible on an exterior of the housing 1101. Pursuant to this, the device 1100 can include electronic components, such as a controller 1119, to control operation of one or more of the drug delivery components. Of course, it will be understood that some components can be disposed partially or entirely above or below the horizontal plane P extending generally centrally through the housing 1101 and still be considered to have a horizontally oriented configuration. Suitable drive mechanisms include, but are not limited to, springs, gas sources, phase changing materials, motors, or other electro-mechanical systems. Example on body injector devices are described in U.S. Ser. No. 62/536,911, filed Jul. 25, 2017, which is hereby incorporated by reference herein.

Given the spread out, horizontal orientation of the components and the low-profile nature of the housing 1101, the devices 1100 of these versions have a relatively large skin contact area, which is used by conventional devices for an adhesive to adhere the on body injector to the skin of the user for subsequent hands-free operation. Advantageously, devices disclosed herein, have a hybrid functionality optionally providing aid to a user with an adhesive contact surface so that the devices grip the user's skin and/or by being affixed about an appendix of the user using, for example, a fastener. This provides aid to users having limited dexterity who may be unable to position and hold the device 1100 during an injection operation without resorting to hands-free operation.

Figure 12:
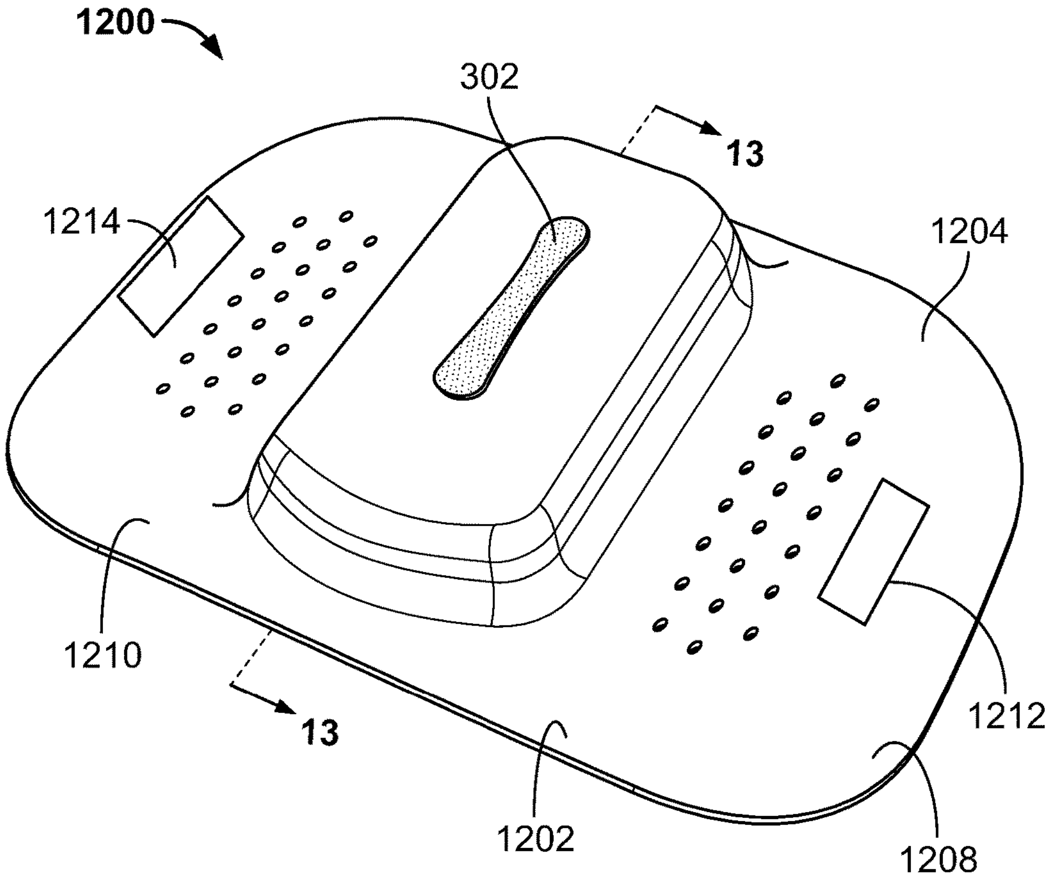
FIG. 12 illustrates another example delivery device that can be used to implement the teachings of this disclosure, where the delivery device of FIG. 12 includes example wraps structured to couple the delivery device adjacent skin during an injection procedure.

FIG. 12 illustrates an isometric view of yet still another example delivery device 1200 that can be used to administer injections in accordance with the teachings of this disclosure. In the illustrated example, the delivery device 1200 includes a body 1202 having a non-cylindrical shape with an example base 1204 and an example handle 1302 (FIG. 13) received by the base 1204. As shown in the cross-sectional view of FIG. 13, the body 1202 carries the actuator 302 and defines a cavity 1304 that houses or otherwise receives the handle 1302 and the drug delivery components (see FIG. 11). In other words, in some examples, the handle 1302 and the body 1202 are removably coupled. While in some examples the handle 1302 and the drug delivery components are embedded in the cavity 1304, in other examples, the handle and the drug delivery components may be selectively received within the cavity 1304 such that the body 1202 can be repeatedly used during different injection procedures.

Figure 13:
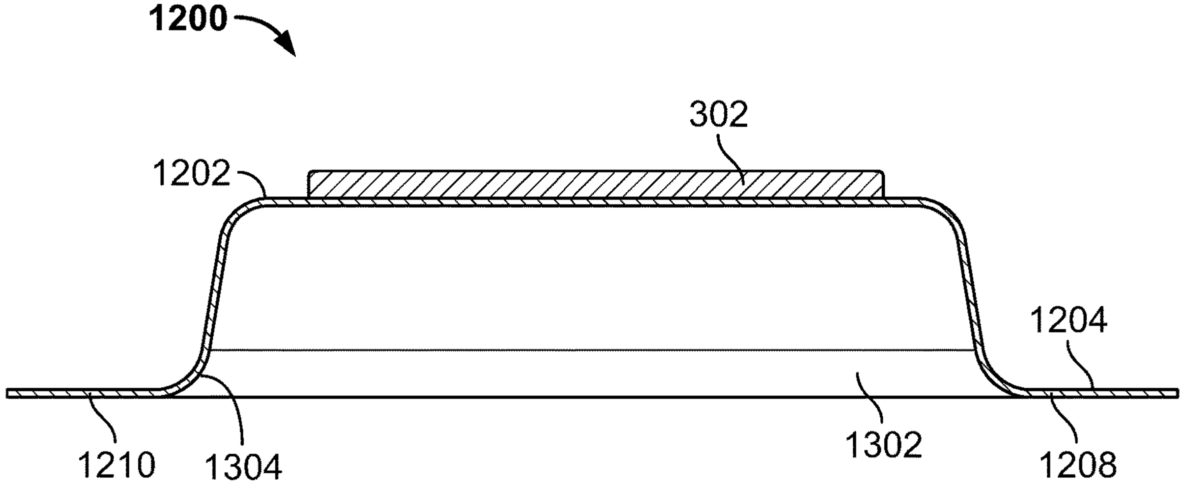
FIG. 13 illustrates a cross-sectional view of the delivery device of FIG. 12 taken along line A-A.

In contrast to some of the other examples disclosed, the delivery device 1200 of FIGS. 12 and 13 is structured to be worn by the user during an injection procedure. As such, the base 1204 includes first and second wraps 1208, 1210 that extend from the cavity 1304. To enable the delivery device 1200 to be coupled to an appendage and/or to another part of a user, the example wraps 1208, 1210 include one or more fasteners 1212, 1214. In some examples, the fasteners 1212, 1214 are implemented by hook-and-loop fasteners, clasps and/or a self-adherent material. Of course, the fasteners 1212, 1214 can be implemented in any other way.

Figure 14:
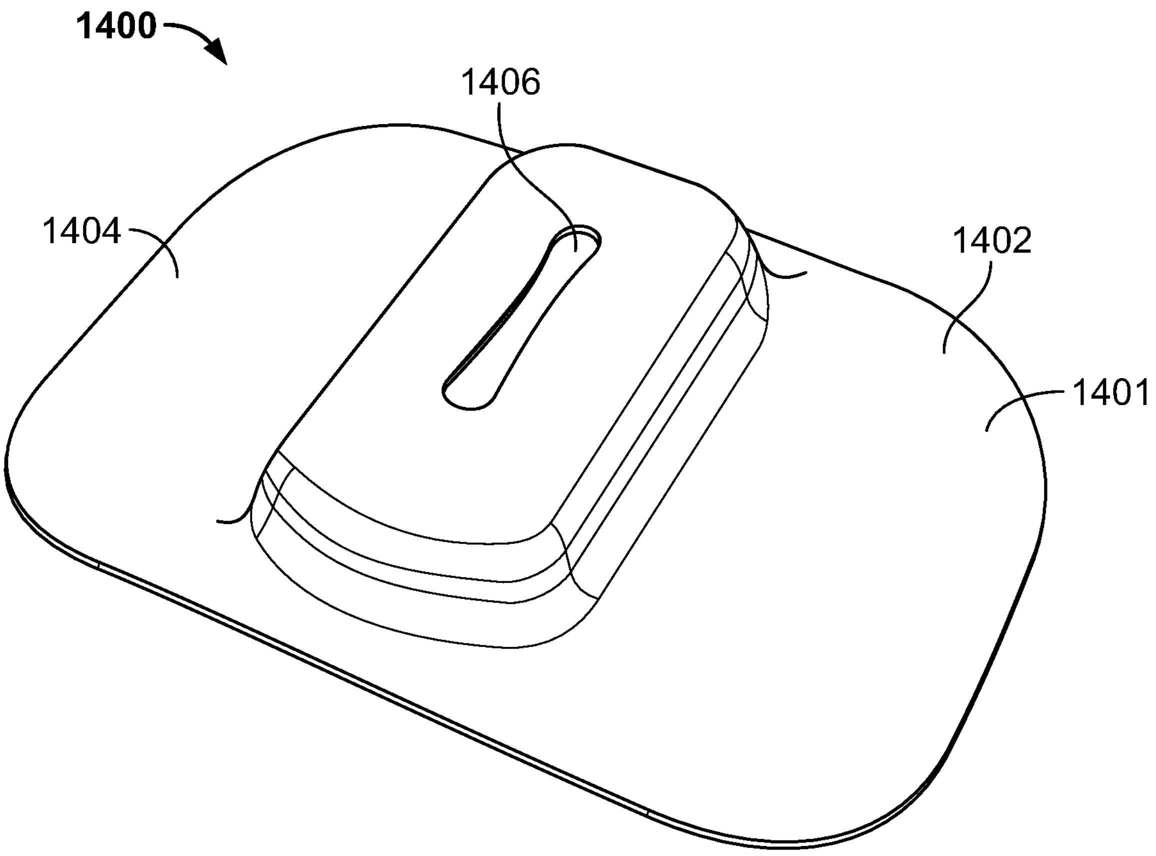
FIG. 14 illustrates an example base of an example delivery device that can be used to implement the teachings of this disclosure.
Figure 15:
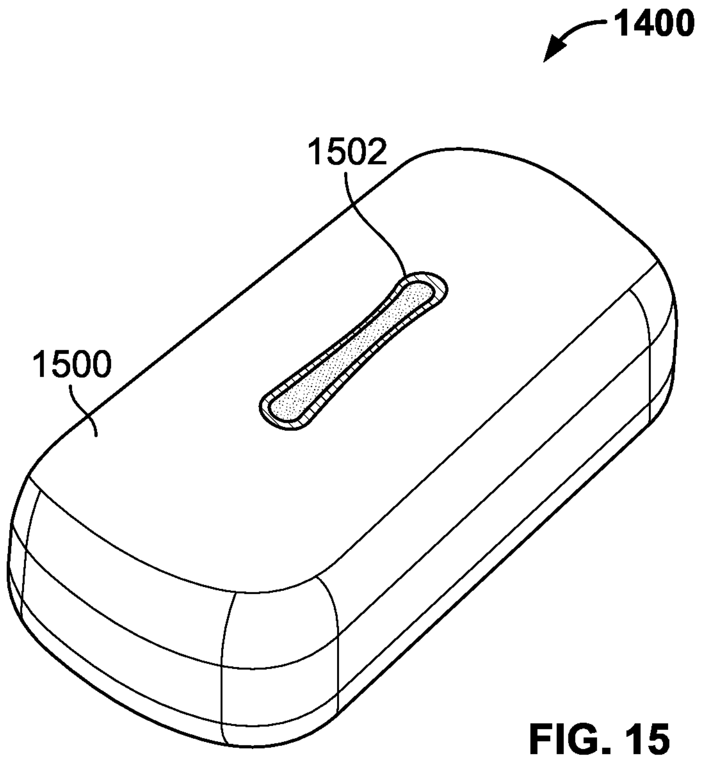
FIG. 15 illustrates an example handle of an example delivery device that is structured to be received by the example base of FIG. 14.

FIGS. 14 and 15 illustrate isometric views of yet still another example delivery device 1400 that is similar to the delivery device 1200 of FIGS. 12 and 13. As shown, FIG. 14 illustrates an example base 1401 including first and second wraps 1402, 1404 and an example aperture 1406 to enable access to a button, inspection window and/or lights of the handle shown in FIG. 15.

FIG. 15 illustrates an example handle 1500 of the example delivery device 1400 that carries drug delivery components (FIG. 1) and includes an example display or a button 1502. In some examples, the button 1502 is a protrusion that extends into the aperture 1406 such that a top surface of the button 1502 and a surrounding surface of the base 1401 are substantially flush when the handle 1500 is received by the base 1401. In this example, the handle 1500 is structured to be received by a cavity of the wraps 1402, 1404 of FIG. 14. Because the base 1401 and the handle 1500 are shown as separate devices, a user can reuse the base 1401 during different injection procedures.

The examples disclosed herein relate to example delivery devices for administering drugs having example form factors that are structured to improve the ability of the user to grip and hold the device against the skin for a threshold amount of time. Such form factors increase an ease of use even when the user has dexterity challenges. In some examples, the delivery devices are implemented as autoinjectors (e.g., hybrid autoinjectors) that are structured to be handheld when an injection is being performed and/or affixed to, for example, an appendage of the body when an injection is being performed.

The drug delivery devices disclosed herein provide hybrid forms that advantageously provide users with additional functionalities as compared to conventional devices. In some examples, the drug delivery devices have co-axial drug delivery components such that a drug reservoir, plunger mechanism and/or needle are axially aligned. The drug delivery devices disclosed herein provide stability, gripping and/or adhesion functionalities typically associated with low profile drug delivery devices to aid users in orienting and/or supporting the device during an injection operation.

When the delivery devices are implemented as an example handheld device, in some examples, the delivery devices include an example handle and a base including a flange that is structured to create suction against the skin without adhesive or with a limited amount of adhesive. Creating suction between the delivery device and the skin reduces the likelihood that the delivery device is moved when administering an injection. To enable suction to be created against the skin, in some examples, the flange has a concave cross-section and is made of rubber, a soft material and/or an elastomer. To enable visual access to the injection area on the skin, in some examples, the base is translucent. However, the base and/or the body of the delivery device may have any other color and/or may include any material or materials. To deter contamination of the contents of the delivery device (e.g., the needle), in some examples, the base of the delivery device includes a seal that is breakable and/or penetratable when the delivery device is activated and/or when an injection procedure is taking place. Alternatively, the seal may be removed prior to an injection taking place.

In other examples, the handheld delivery device is structured to be received by an example cradle that is held against the skin by the user using, for example, flanges of the cradle. However, the cradle may be held in place in any other way. For example, the cradle may include adhesive and/or may be structured to form a vacuum and/or a suction connection with the skin. Regardless of how the cradle is held in place during an injection procedure, the cradle may be made of a translucent material, rubber, elastomer and/or another soft material. As with some of the other disclosed examples, the cradle may include a seal that is removable (e.g., a release liner) prior to an injection procedure occurring and/or is penetrable by the needle during the injection procedure.

To guide the position of the delivery device using the example cradles, in some examples, the cradle is sized and/or shaped to be loosely held by the administrator of the injection (e.g., the user) while the an end of the delivery device is moved toward the skin. For example, the cradle may define an aperture having conical walls that encourage and/or guide the delivery device toward the delivery site on the skin. To enable the contents of the delivery device to be visually accessed, in some examples, a handle of the delivery device includes a window this is recessed relative to a surrounding portion of the handle. An interface between the window and the surrounding portion of the handle may be chamfered.

In other examples, the handheld delivery device includes an example lid that is structured to assist in positioning the delivery device relative to the skin during an injection procedure and/or is structured to increase an effective contact area between the delivery device and the injection area. In some examples, the lid is attached to a body of the delivery device via an example living hinge. The living hinge may be sized to enable the lid to rotate approximately 180° and to provide support for the body of the delivery device to deter the delivery device from moving and/or wobbling during an injection procedure. For example, the lid and/or the body of the delivery device may be structured to interact to position the delivery device at approximately a 90° angle relative to the skin. As set forth herein, the phrase "approximately 900" means+/−5° of 90°. While the delivery device is mentioned being positioned at approximately 90° relative to the skin when an injection is being administered, the delivery device can be positioned at any other position.

In other examples, the lid and/or the body of the delivery device are structured to be coupled to the delivery device using a fastener when an injection procedure is taking place. The fastener may be a snap connection or any other type of fastener (e.g., adhesive, a hook-and-loop fastener). To further reduce the likelihood that the delivery device moves and/or wobbles when an injection is being administered, in some examples, the lid and/or the body of the delivery device can include adhesive or a non-adhesive non-slip coating (e.g., runner, elastomer, silicone, etc.).

In other examples, the example handheld delivery device includes example sides that are structured to pinch the skin adjacent an injection area prior to an injection taking place. To further encourage the sides of the delivery device to pinch the skin, inner facing surfaces and/or ends/arms of the delivery device may include an adhesive and/or non-slip coating. In some such examples, the sides of the delivery device are flexible to enable the sides to move from a non-pinching position to a pinching position. While the arms may inwardly move any distance, in some examples, a distance moved by one of the arms between non-pinching position and the pinching position is between about 0.5 centimeters (cm) and about 3 cm. Additionally, in some examples, moving the arms from the non-pinching position to the pinching position actuates an actuator that causes an example needle to extend from the bottom of the delivery device and/or for contents (e.g., drugs) of the delivery device to be dispensed through the needle.

In examples in which the delivery devices are structured to be carried by the body (e.g., on a leg) during an injection procedure, the delivery device is structured to be housed in an example band. The band may be structured as an arm band, a leg band, etc. In some such examples, the band is an arm band including a cavity to receive an example syringe assembly. While the band may be coupled to the body in any suitable way, in some examples, the band is coupled using a fastener such as, for example, a hook-and-loop fastener, clasps and/or a self-adherent wrap material.

Regardless of the form factor that the delivery device has, in some examples, the delivery device includes an example syringe assembly having an example barrel that receives a plunger. In some examples, the delivery device includes an example first drive structured to move the plunger to dispense contents of the barrel. In some examples, the first drive and/or another drive is structured to move a needle of the syringe assembly from a retracted position to a deployed position. The first and/or second drives may be actuated in different ways. For example, the delivery device may carry a button that is pressed by the user and/or the drives may be activated when a threshold amount of pressure is applied at the base of the delivery device and/or when a threshold amount of pressure is applied to the sides of the delivery device.

In other examples, a needle guard is movable from an extended position in which the needle guard covers the needle to a retracted position where the need guard uncovers and/or exposes the needle. The needle guard may move from the extended position to the retracted position when a threshold amount of force is applied to the needle guard. The barrel may be referred to as a container and/or a reservoir. The needle may be associated with a cannula.

It will be appreciated that elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments. The same reference numbers may be used to describe like or similar parts. Further, while several examples have been disclosed herein, any features from any examples may be combined with or replaced by other features from other examples. Moreover, while several examples have been disclosed herein, changes may be made to the disclosed examples within departing from the scope of the claims.

The above description describes various assemblies, devices, and methods for use with a drug delivery device. It should be clear that the assemblies, drug delivery devices, or methods can further comprise use of a medicament listed below with the caveat that the following list should neither be considered to be all inclusive nor limiting. The medicament will be contained in a reservoir. In some instances, the reservoir is a primary container that is either filled or pre-filled for treatment with the medicament. The primary container can be a cartridge or a pre-filled syringe.

For example, the drug delivery device or more specifically the reservoir of the device may be filled with colony stimulating factors, such as granulocyte colony-stimulating factor (G-CSF). Such G-CSF agents include, but are not limited to, Neupogen® (filgrastim) and Neulasta® (pegfilgrastim). In various other embodiments, the drug delivery device may be used with various pharmaceutical products, such as an erythropoiesis stimulating agent (ESA), which may be in a liquid or a lyophilized form. An ESA is any molecule that stimulates erythropoiesis, such as Epogen® (epoetin alfa), Aranesp® (darbepoetin alfa), Dynepo® (epoetin delta), Mircera® (methyoxy polyethylene glycol-epoetin beta), Hematide®, MRK-2578, INS-22, Retacrit® (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epoetin theta), epoetin alfa, epoetin beta, epoetin zeta, epoetin theta, and epoetin delta, as well as the molecules or variants or analogs thereof as disclosed in the following patents or patent applications, each of which is herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,986,047; 6,583,272; 7,084,245; and 7,271,689; and PCT Publication Nos. WO 91/05867; WO 95/05465; WO 96/40772; WO 00/24893; WO 01/81405; and WO 2007/136752.

An ESA can be an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, epoetin alfa, epoetin beta, epoetin delta, epoetin omega, epoetin iota, epoetin zeta, and analogs thereof, pegylated erythropoietin, carbamylated erythropoietin, mimetic peptides (including EMP1/hematide), and mimetic antibodies. Exemplary erythropoiesis stimulating proteins include erythropoietin, darbepoetin, erythropoietin agonist variants, and peptides or antibodies that bind and activate erythropoietin receptor (and include compounds reported in U.S. Publication Nos. 2003/0215444 and 2006/0040858, the disclosures of each of which is incorporated herein by reference in its entirety) as well as erythropoietin molecules or variants or analogs thereof as disclosed in the following patents or patent applications, which are each herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,830,851; 5,856,298; 5,986,047; 6,030,086; 6,310,078; 6,391,633; 6,583,272; 6,586,398; 6,900,292; 6,750,369; 7,030,226; 7,084,245; and 7,217,689; U.S. Publication Nos. 2002/0155998; 2003/0077753; 2003/0082749; 2003/0143202; 2004/0009902; 2004/0071694; 2004/0091961; 2004/0143857; 2004/0157293; 2004/0175379; 2004/0175824; 2004/0229318; 2004/0248815; 2004/0266690; 2005/0019914; 2005/0026834; 2005/0096461; 2005/0107297; 2005/0107591; 2005/0124045; 2005/0124564; 2005/0137329; 2005/0142642; 2005/0143292; 2005/0153879; 2005/0158822; 2005/0158832; 2005/0170457; 2005/0181359; 2005/0181482; 2005/0192211; 2005/0202538; 2005/0227289; 2005/0244409; 2006/0088906; and 2006/0111279; and PCT Publication Nos. WO 91/05867; WO 95/05465; WO 99/66054; WO 00/24893; WO 01/81405; WO 00/61637; WO 01/36489; WO 02/014356; WO 02/19963; WO 02/20034; WO 02/49673; WO 02/085940; WO 03/029291; WO 2003/055526; WO 2003/084477; WO 2003/094858; WO 2004/002417; WO 2004/002424; WO 2004/009627; WO 2004/024761; WO 2004/033651; WO 2004/035603; WO 2004/043382; WO 2004/101600; WO 2004/101606; WO 2004/101611; WO 2004/106373; WO 2004/018667; WO 2005/001025; WO 2005/001136; WO 2005/021579; WO 2005/025606; WO 2005/032460; WO 2005/051327; WO 2005/063808; WO 2005/063809; WO 2005/070451; WO 2005/081687; WO 2005/084711; WO 2005/103076; WO 2005/100403; WO 2005/092369; WO 2006/50959; WO 2006/02646; and WO 2006/29094.

Examples of other pharmaceutical products for use with the device may include, but are not limited to, antibodies such as Vectibix® (panitumumab), Xgeva™ (denosumab) and Prolia™ (denosamab); other biological agents such as Enbrel® (etanercept, TNF-receptor/Fc fusion protein, TNF blocker), Neulasta® (pegfilgrastim, pegylated filgastrim, pegylated G-CSF, pegylated hu-Met-G-CSF), Neupogen® (filgrastim, G-CSF, hu-MetG-CSF), and Nplate® (romiplostim); small molecule drugs such as Sensipar® (cinacalcet). The device may also be used with a therapeutic antibody, a polypeptide, a protein or other chemical, such as an iron, for example, ferumoxytol, iron dextrans, ferric glyconate, and iron sucrose. The pharmaceutical product may be in liquid form, or reconstituted from lyophilized form.

Among particular illustrative proteins are the specific proteins set forth below, including fusions, fragments, analogs, variants or derivatives thereof:

OPGL specific antibodies, peptibodies, and related proteins, and the like (also referred to as RANKL specific antibodies, peptibodies and the like), including fully humanized and human OPGL specific antibodies, particularly fully humanized monoclonal antibodies, including but not limited to the antibodies described in PCT Publication No. WO 03/002713, which is incorporated herein in its entirety as to OPGL specific antibodies and antibody related proteins, particularly those having the sequences set forth therein, particularly, but not limited to, those denoted therein: 9H7; 18B2; 2D8; 2E11; 16E1; and 22B3, including the OPGL specific antibodies having either the light chain of SEQ ID NO:2 as set forth therein in FIG. 2 and/or the heavy chain of SEQ ID NO:4, as set forth therein in FIG. 4, each of which is individually and specifically incorporated by reference herein in its entirety fully as disclosed in the foregoing publication;

Myostatin binding proteins, peptibodies, and related proteins, and the like, including myostatin specific peptibodies, particularly those described in U.S. Publication No. 2004/0181033 and PCT Publication No. WO 2004/058988, which are incorporated by reference herein in their entirety particularly in parts pertinent to myostatin specific peptibodies, including but not limited to peptibodies of the mTN8-19 family, including those of SEQ ID NOS: 305-351, including TN8-19-1 through TN8-19-40, TN8-19 con1 and TN8-19 con2; peptibodies of the mL2 family of SEQ ID NOS: 357-383; the mL15 family of SEQ ID NOS: 384-409; the mL17 family of SEQ ID NOS: 410-438; the mL20 family of SEQ ID NOS: 439-446; the mL21 family of SEQ ID NOS: 447-452; the mL24 family of SEQ ID NOS: 453-454; and those of SEQ ID NOS: 615-631, each of which is individually and specifically incorporated by reference herein in their entirety fully as disclosed in the foregoing publication;

IL-4 receptor specific antibodies, peptibodies, and related proteins, and the like, particularly those that inhibit activities mediated by binding of IL-4 and/or IL-13 to the receptor, including those described in PCT Publication No. WO 2005/047331 or PCT Application No. PCT/US2004/37242 and in U.S. Publication No. 2005/112694, which are incorporated herein by reference in their entirety particularly in parts pertinent to IL-4 receptor specific antibodies, particularly such antibodies as are described therein, particularly, and without limitation, those designated therein: L1H1; L1H2; L1H3; L1H4; L1H5; L1H6; L1H7; L1H8; L1H9;

L1H10; L1H11; L2H1; L2H2; L2H3; L2H4; L2H5; L2H6; L2H7; L2H8; L2H9; L2H10; L2H11; L2H12; L2H13; L2H14; L3H1; L4H1; L5H1; L6H1, each of which is individually and specifically incorporated by reference herein in its entirety fully as disclosed in the foregoing publication;

Interleukin 1-receptor 1 ("IL1-R1") specific antibodies, peptibodies, and related proteins, and the like, including but not limited to those described in U.S. Publication No. 2004/097712, which is incorporated herein by reference in its entirety in parts pertinent to IL1-R1 specific binding proteins, monoclonal antibodies in particular, especially, without limitation, those designated therein: 15CA, 26F5, 27F2, 24E12, and 10H7, each of which is individually and specifically incorporated by reference herein in its entirety fully as disclosed in the aforementioned publication;

Ang2 specific antibodies, peptibodies, and related proteins, and the like, including but not limited to those described in PCT Publication No. WO 03/057134 and U.S. Publication No. 2003/0229023, each of which is incorporated herein by reference in its entirety particularly in parts pertinent to Ang2 specific antibodies and peptibodies and the like, especially those of sequences described therein and including but not limited to: L1(N); L1(N) WT; L1(N) 1K WT; 2xL1(N); 2xL1(N) WT; Con4 (N), Con4 (N) 1K WT, 2xCon4 (N) 1K; L1C; L1C 1K; 2xL1C; Con4C; Con4C 1K; 2xCon4C 1K; Con4-L1(N); Con4-L1C; TN-12-9 (N); C17 (N); TN8-8 (N); TN8-14 (N); Con 1 (N), also including anti-Ang 2 antibodies and formulations such as those described in PCT Publication No. WO 2003/030833 which is incorporated herein by reference in its entirety as to the same, particularly Ab526; Ab528; Ab531; Ab533; Ab535; Ab536; Ab537; Ab540; Ab543; Ab544; Ab545; Ab546; A551; Ab553; Ab555; Ab558; Ab559; Ab565; AbF1AbFD; AbFE; AbFJ; AbFK; AbG1D4; AbGC1E8; AbH1C12; AbIA1; AbIF; AbIK, AbIP; and AbIP, in their various permutations as described therein, each of which is individually and specifically incorporated by reference herein in its entirety fully as disclosed in the foregoing publication;

NGF specific antibodies, peptibodies, and related proteins, and the like including, in particular, but not limited to those described in U.S. Publication No. 2005/0074821 and U.S. Pat. No. 6,919,426, which are incorporated herein by reference in their entirety particularly as to NGF-specific antibodies and related proteins in this regard, including in particular, but not limited to, the NGF-specific antibodies therein designated 4D4, 4G6, 6H9, 7H2, 14D10 and 14D11, each of which is individually and specifically incorporated by reference herein in its entirety fully as disclosed in the foregoing publication;

CD22 specific antibodies, peptibodies, and related proteins, and the like, such as those described in U.S. Pat. No. 5,789,554, which is incorporated herein by reference in its entirety as to CD22 specific antibodies and related proteins, particularly human CD22 specific antibodies, such as but not limited to humanized and fully human antibodies, including but not limited to humanized and fully human monoclonal antibodies, particularly including but not limited to human CD22 specific IgG antibodies, such as, for instance, a dimer of a human-mouse monoclonal hLL2 gamma-chain disulfide linked to a human-mouse monoclonal hLL2 kappa-chain, including, but limited to, for example, the human CD22 specific fully humanized antibody in Epratuzumab, CAS registry number 501423-23-0;

IGF-1 receptor specific antibodies, peptibodies, and related proteins, and the like, such as those described in PCT Publication No. WO 06/069202, which is incorporated herein by reference in its entirety as to IGF-1 receptor specific antibodies and related proteins, including but not limited to the IGF-1 specific antibodies therein designated L1H1, L2H2, L3H3, L4H4, L5H5, L6H6, L7H7, L8H8, L9H9, L10H10, L11H11, L12H12, L13H13, L14H14, L15H15, L16H16, L17H17, L18H18, L19H19, L20H20, L21H21, L22H22, L23H23, L24H24, L25H25, L26H26, L27H27, L28H28, L29H29, L30H30, L31H31, L32H32, L33H33, L34H34, L35H35, L36H36, L37H37, L38H38, L39H39, L40H40, L41H41, L42H42, L43H43, L44H44, L45H45, L46H46, L47H47, L48H48, L49H49, L50H50, L51H51, L52H52, and IGF-1R-binding fragments and derivatives thereof, each of which is individually and specifically incorporated by reference herein in its entirety fully as disclosed in the foregoing publication;

Also among non-limiting examples of anti-IGF-1R antibodies for use in the methods and compositions of the present invention are each and all of those described in:

(i) U.S. Publication No. 2006/0040358 (published Feb. 23, 2006), 2005/0008642 (published Jan. 13, 2005), 2004/0228859 (published Nov. 18, 2004), including but not limited to, for instance, antibody 1A (DSMZ Deposit No. DSM ACC 2586), antibody 8 (DSMZ Deposit No. DSM ACC 2589), antibody 23 (DSMZ Deposit No. DSM ACC 2588) and antibody 18 as described therein;

(ii) PCT Publication No. WO 06/138729 (published Dec. 28, 2006) and WO 05/016970 (published Feb. 24, 2005), and Lu et al. (2004), J. Biol. Chem. 279:2856-2865, including but not limited to antibodies 2F8, A12, and IMC-A12 as described therein;

(iii) PCT Publication No. WO 07/012614 (published Feb. 1, 2007), WO 07/000328 (published Jan. 4, 2007), WO 06/013472 (published Feb. 9, 2006), WO 05/058967 (published Jun. 30, 2005), and WO 03/059951 (published Jul. 24, 2003);

(iv) U.S. Publication No. 2005/0084906 (published Apr. 21, 2005), including but not limited to antibody 7C10, chimaeric antibody C7C10, antibody h7C10, antibody 7H2M, chimaeric antibody *7C10, antibody GM 607, humanized antibody 7C10 version 1, humanized antibody 7C10 version 2, humanized antibody 7C10 version 3, and antibody 7H2HM, as described therein;

(v) U.S. Publication Nos. 2005/0249728 (published Nov. 10, 2005), 2005/0186203 (published Aug. 25, 2005), 2004/0265307 (published Dec. 30, 2004), and 2003/0235582 (published Dec. 25, 2003) and Maloney et al. (2003), Cancer Res. 63:5073-5083, including but not limited to antibody EM164, resurfaced EM164, humanized EM164, huEM164 v1.0, huEM164 v1.1, huEM164 v1.2, and huEM164 v1.3 as described therein;

(vi) U.S. Pat. No. 7,037,498 (issued May 2, 2006), U.S. Publication Nos. 2005/0244408 (published Nov. 30, 2005) and 2004/0086503 (published May 6, 2004), and Cohen, et al. (2005), Clinical Cancer Res. 11:2063-2073, e.g., antibody CP-751,871, including but not limited to each of the antibodies produced by the hybridomas having the ATCC accession numbers PTA-2792, PTA-2788, PTA-2790, PTA-2791, PTA-2789, PTA-2793, and antibodies 2.12.1, 2.13.2, 2.14.3, 3.1.1, 4.9.2, and 4.17.3, as described therein;

(vii) U.S. Publication Nos. 2005/0136063 (published Jun. 23, 2005) and 2004/0018191 (published Jan. 29, 2004), including but not limited to antibody 19D12 and an antibody comprising a heavy chain encoded by a polynucleotide in plasmid 15H12/19D12 HCA (γ4), deposited at the ATCC under number PTA-5214, and a light chain encoded by a polynucleotide in plasmid 15H12/19D12 LCF (K), deposited at the ATCC under number PTA-5220, as described therein; and (viii) U.S. Publication No. 2004/0202655 (published Oct. 14, 2004), including but not limited to antibodies PINT-6A1, PINT-7A2, PINT-7A4, PINT-7A5, PINT-7A6, PINT-8A1, PINT-9A2, PINT-11A1, PINT-11A2, PINT-11A3, PINT-11A4, PINT-11A5, PINT-11A7, PINT-11A12, PINT-12A1, PINT-12A2, PINT-12A3, PINT-12A4, and PINT-12A5, as described therein; each and all of which are herein incorporated by reference in their entireties, particularly as to the aforementioned antibodies, peptibodies, and related proteins and the like that target IGF-1 receptors;

B-7 related protein 1 specific antibodies, peptibodies, related proteins and the like ("B7RP-1," also is referred to in the literature as B7H2, ICOSL, B7h, and CD275), particularly B7RP-specific fully human monoclonal IgG2 antibodies, particularly fully human IgG2 monoclonal antibody that binds an epitope in the first immunoglobulin-like domain of B7RP-1, especially those that inhibit the interaction of B7RP-1 with its natural receptor, ICOS, on activated T cells in particular, especially, in all of the foregoing regards, those disclosed in U.S. Publication No. 2008/0166352 and PCT Publication No. WO 07/011941, which are incorporated herein by reference in their entireties as to such antibodies and related proteins, including but not limited to antibodies designated therein as follow: 16H (having light chain variable and heavy chain variable sequences SEQ ID NO:1 and SEQ ID NO:7 respectively therein); 5D (having light chain variable and heavy chain variable sequences SEQ ID NO:2 and SEQ ID NO: 9 respectively therein); 2H (having light chain variable and heavy chain variable sequences SEQ ID NO:3 and SEQ ID NO: 10 respectively therein); 43H (having light chain variable and heavy chain variable sequences SEQ ID NO:6 and SEQ ID NO: 14 respectively therein); 41H (having light chain variable and heavy chain variable sequences SEQ ID NO:5 and SEQ ID NO: 13 respectively therein); and 15H (having light chain variable and heavy chain variable sequences SEQ ID NO:4 and SEQ ID NO: 12 respectively therein), each of which is individually and specifically incorporated by reference herein in its entirety fully as disclosed in the foregoing publication;

IL-15 specific antibodies, peptibodies, and related proteins, and the like, such as, in particular, humanized monoclonal antibodies, particularly antibodies such as those disclosed in U.S. Publication Nos. 2003/0138421; 2003/023586; and 2004/0071702; and U.S. Pat. No. 7,153,507, each of which is incorporated herein by reference in its entirety as to IL-15 specific antibodies and related proteins, including peptibodies, including particularly, for instance, but not limited to, HuMax IL-15 antibodies and related proteins, such as, for instance, 146B7;

IFN gamma specific antibodies, peptibodies, and related proteins and the like, especially human IFN gamma specific antibodies, particularly fully human anti-IFN gamma antibodies, such as, for instance, those described in U.S. Publication No. 2005/0004353, which is incorporated herein by reference in its entirety as to IFN gamma specific antibodies, particularly, for example, the antibodies therein designated 1118; 1118*; 1119; 1121; and 1121*. The entire sequences of the heavy and light chains of each of these antibodies, as well as the sequences of their heavy and light chain variable regions and complementarity determining regions, are each individually and specifically incorporated by reference herein in its entirety fully as disclosed in the foregoing publication and in Thakur et al. (1999), Mol. Immunol. 36:1107-1115. In addition, description of the properties of these antibodies provided in the foregoing publication is also incorporated by reference herein in its entirety. Specific antibodies include those having the heavy chain of SEQ ID NO: 17 and the light chain of SEQ ID NO: 18; those having the heavy chain variable region of SEQ ID NO:6 and the light chain variable region of SEQ ID NO:8; those having the heavy chain of SEQ ID NO: 19 and the light chain of SEQ ID NO:20; those having the heavy chain variable region of SEQ ID NO: 10 and the light chain variable region of SEQ ID NO: 12; those having the heavy chain of SEQ ID NO:32 and the light chain of SEQ ID NO:20; those having the heavy chain variable region of SEQ ID NO:30 and the light chain variable region of SEQ ID NO: 12; those having the heavy chain sequence of SEQ ID NO:21 and the light chain sequence of SEQ ID NO:22; those having the heavy chain variable region of SEQ ID NO: 14 and the light chain variable region of SEQ ID NO: 16; those having the heavy chain of SEQ ID NO:21 and the light chain of SEQ ID NO:33; and those having the heavy chain variable region of SEQ ID NO: 14 and the light chain variable region of SEQ ID NO: 31, as disclosed in the foregoing publication. A specific antibody contemplated is antibody 1119 as disclosed in the foregoing U.S. publication and having a complete heavy chain of SEQ ID NO: 17 as disclosed therein and having a complete light chain of SEQ ID NO: 18 as disclosed therein;

TALL-1 specific antibodies, peptibodies, and the related proteins, and the like, and other TALL specific binding proteins, such as those described in U.S. Publication Nos. 2003/0195156 and 2006/0135431, each of which is incorporated herein by reference in its entirety as to TALL-1 binding proteins, particularly the molecules of Tables 4 and 5B, each of which is individually and specifically incorporated by reference herein in its entirety fully as disclosed in the foregoing publications;

Parathyroid hormone ("PTH") specific antibodies, peptibodies, and related proteins, and the like, such as those described in U.S. Pat. No. 6,756,480, which is incorporated herein by reference in its entirety, particularly in parts pertinent to proteins that bind PTH;

Thrombopoietin receptor ("TPO-R") specific antibodies, peptibodies, and related proteins, and the like, such as those described in U.S. Pat. No. 6,835,809, which is herein incorporated by reference in its entirety, particularly in parts pertinent to proteins that bind TPO-R;

Hepatocyte growth factor ("HGF") specific antibodies, peptibodies, and related proteins, and the like, including those that target the HGF/SF: cMet axis (HGF/SF: c-Met), such as the fully human monoclonal antibodies that neutralize hepatocyte growth factor/scatter (HGF/SF) described in U.S. Publication No. 2005/0118643 and PCT Publication No. WO 2005/017107, huL2G7 described in U.S. Pat. No. 7,220,410 and OA-5d5 described in U.S. Pat. Nos. 5,686,292 and 6,468,529 and in PCT Publication No. WO 96/38557, each of which is incorporated herein by reference in its entirety, particularly in parts pertinent to proteins that bind HGF;

TRAIL-R2 specific antibodies, peptibodies, related proteins and the like, such as those described in U.S. Pat. No. 7,521,048, which is herein incorporated by reference in its entirety, particularly in parts pertinent to proteins that bind TRAIL-R2;

Activin A specific antibodies, peptibodies, related proteins, and the like, including but not limited to those described in U.S. Publication No. 2009/0234106, which is herein incorporated by reference in its entirety, particularly in parts pertinent to proteins that bind Activin A;

TGF-beta specific antibodies, peptibodies, related proteins, and the like, including but not limited to those described in U.S. Pat. No. 6,803,453 and U.S. Publication No. 2007/0110747, each of which is herein incorporated by reference in its entirety, particularly in parts pertinent to proteins that bind TGF-beta;

Amyloid-beta protein specific antibodies, peptibodies, related proteins, and the like, including but not limited to those described in PCT Publication No. WO 2006/081171, which is herein incorporated by reference in its entirety, particularly in parts pertinent to proteins that bind amyloid-beta proteins. One antibody contemplated is an antibody having a heavy chain variable region comprising SEQ ID NO:8 and a light chain variable region having SEQ ID NO:6 as disclosed in the foregoing publication;

c-Kit specific antibodies, peptibodies, related proteins, and the like, including but not limited to those described in U.S. Publication No. 2007/0253951, which is incorporated herein by reference in its entirety, particularly in parts pertinent to proteins that bind c-Kit and/or other stem cell factor receptors;

OX40L specific antibodies, peptibodies, related proteins, and the like, including but not limited to those described in U.S. Publication No. 2006/0002929, which is incorporated herein by reference in its entirety, particularly in parts pertinent to proteins that bind OX40L and/or other ligands of the OX40 receptor; and Other exemplary proteins, including Activase® (alteplase, tPA); Aranesp® (darbepoetin alfa); Epogen® (epoetin alfa, or erythropoietin); GLP-1, Avonex® (interferon beta-1a); Bexxar® (tositumomab, anti-CD22 monoclonal antibody); Betaseron® (interferon-beta); Campath® (alemtuzumab, anti-CD52 monoclonal antibody); Dynepo® (epoetin delta); Velcade® (bortezomib); MLN0002 (anti-α4β7 mAb); MLN1202 (anti-CCR2 chemokine receptor mAb); Enbrel® (etanercept, TNF-receptor/Fc fusion protein, TNF blocker); Eprex® (epoetin alfa); Erbitux® (cetuximab, anti-EGFR/HER1/c-ErbB-1); Genotropin® (somatropin, Human Growth Hormone); Herceptin® (trastuzumab, anti-HER2/neu (erbB2) receptor mAb); Humatrope® (somatropin, Human Growth Hormone); Humira® (adalimumab); insulin in solution; Infergen® (interferon alfacon-1); Natrecor® (nesiritide; recombinant human B-type natriuretic peptide (hBNP); Kineret® (anakinra); Leukine® (sargamostim, rhuGM-CSF); LymphoCide® (epratuzumab, anti-CD22 mAb); Benlysta™ (lymphostat B, belimumab, anti-BlyS mAb); Metalyse® (tenecteplase, t-PA analog); Mircera® (methoxy polyethylene glycol-epoetin beta); Mylotarg® (gemtuzumab ozogamicin); Raptiva® (efalizumab); Cimzia® (certolizumab pegol, CDP 870); Soliris™ (eculizumab); pexelizumab (anti-C5 complement); Numax® (MEDI-524); Lucentis® (ranibizumab); Panorex® (17-1A, edrecolomab); Trabio® (lerdelimumab); TheraCim hR3 (nimotuzumab); Omnitarg (pertuzumab, 2C4); Osidem® (IDM-1); OvaRex® (B43.13); Nuvion® (visilizumab); cantuzumab mertansine (huC242-DM1); NeoRecormon® (epoetin beta); Neumega® (oprelvekin, human interleukin-11); Neulasta® (pegylated filgastrim, pegylated G-CSF, pegylated hu-Met-G-CSF); Neupogen® (filgrastim, G-CSF, hu-MetG-CSF); Orthoclone OKT3® (muromonab-CD3, anti-CD3 monoclonal antibody); Procrit® (epoetin alfa); Remicade® (infliximab, anti-TNFα monoclonal antibody); Reopro® (abciximab, anti-GP IIb/IIia receptor monoclonal antibody); Actemra® (anti-IL6 Receptor mAb); Avastin® (bevacizumab), HuMax-CD4 (zanolimumab); Rituxan® (rituximab, anti-CD20 mAb); Tarceva® (erlotinib); Roferon-A®-(interferon alfa-2a); Simulect® (basiliximab); Prexige® (lumiracoxib); Synagis® (palivizumab); 146B7-CHO (anti-IL 15 antibody, see U.S. Pat. No. 7,153,507); Tysabri® (natalizumab, anti-α4integrin mAb); Valortim® (MDX-1303, anti-*B. anthracis* protective antigen mAb); ABthrax™; Vectibix® (panitumumab); Xolair® (omalizumab); ETI211 (anti-MRSA mAb); IL-1 trap (the Fc portion of human IgG1 and the extracellular domains of both IL-1 receptor components (the Type I receptor and receptor accessory protein)); VEGF trap (lg domains of VEGFR1 fused to IgG1 Fc); Zenapax® (daclizumab); Zenapax® (daclizumab, anti-IL-2Ra mAb); Zevalin® (ibritumomab tiuxetan); Zetia® (ezetimibe); Orencia® (atacicept, TACI-Ig); anti-CD80 monoclonal antibody (galiximab); anti-CD23 mAb (lumiliximab); BR2-Fc (huBR3/huFc fusion protein, soluble BAFF antagonist); CNTO 148 (golimumab, anti-TNFα mAb); HGS-ETR1 (mapatumumab; human anti-TRAIL Receptor-1 mAb); HuMax-CD20 (ocrelizumab, anti-CD20 human mAb); HuMax-EGFR (zalutumumab); M200 (volociximab, anti-α5β1 integrin mAb); MDX-010 (ipilimumab, anti-CTLA-4 mAb and VEGFR-1 (IMC-18F1); anti-BR3 mAb; anti-*C. difficile* Toxin A and Toxin B C mAbs MDX-066 (CDA-1) and MDX-1388); anti-CD22 dsFV-PE38 conjugates (CAT-3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase|Fibrogen (FG-3019); anti-CTLA4 mAb; anti-eotaxin1 mAb (CAT-213); anti-FGF8 mAb; anti-ganglioside GD2 mAb; anti-ganglioside GM2 mAb; anti-GDF-8 human mAb (MYO-029); anti-GM-CSF Receptor mAb (CAM-3001); anti-HepC mAb (HuMax HepC); anti-IFNα mAb (MEDI-545, MDX-1103); anti-IGF1R mAb; anti-IGF-1R mAb (HuMax-Inflam); anti-IL12 mAb (ABT-874); anti-IL12/IL23 mAb (CNTO 1275);

anti-IL13 mAb (CAT-354); anti-IL2Ra mAb (HuMax-TAC); anti-IL5 Receptor mAb; anti-integrin receptors mAb (MDX-018, CNTO 95); anti-IP10 Ulcerative Colitis mAb (MDX-1100); anti-LLY antibody; BMS-66513; anti-Mannose Receptor/hCGB mAb (MDX-1307); anti-mesothelin dsFv-PE38 conjugate (CAT-5001); anti-PD1mAb (MDX-1106 (ONO-4538); anti-PDGFRα antibody (IMC-3G3); anti-TGFβ mAb (GC-1008); anti-TRAIL Receptor-2 human mAb (HGS-ETR2); anti-TWEAK mAb; anti-VEGFR/Flt-1 mAb; anti-ZP3 mAb (HuMax-ZP3); NVS Antibody #1; and NVS Antibody #2.

Also included can be a sclerostin antibody, such as but not limited to romosozumab, blosozumab, or BPS 804 (Novartis). Further included can be therapeutics such as rilotumumab, bixalomer, trebananib, ganitumab, conatumumab, motesanib diphosphate, brodalumab, vidupiprant, panitumumab, denosumab, NPLATE, PROLIA, VECTIBIX or XGEVA. Additionally, included in the device can be a monoclonal antibody (IgG) that binds human Proprotein Convertase Subtilisin/Kexin Type 9 (PCSK9). Such PCSK9 specific antibodies include, but are not limited to, Repatha® (evolocumab) and Praluent® (alirocumab), as well as molecules, variants, analogs or derivatives thereof as disclosed in the following patents or patent applications, each of which is herein incorporated by reference in its entirety for all purposes: U.S. Pat. No. 8,030,547, U.S. Publication No. 2013/0064825, WO2008/057457, WO2008/057458, WO2008/057459, WO2008/063382, WO2008/133647, WO2009/100297, WO2009/100318, WO2011/037791, WO2011/053759, WO2011/053783, WO2008/125623, WO2011/072263, WO2009/055783, WO2012/0544438, WO2010/029513, WO2011/111007, WO2010/077854, WO2012/088313, WO2012/101251, WO2012/101252, WO2012/101253, WO2012/109530, and WO2001/031007.

Also included can be talimogene laherparepvec or another oncolytic HSV for the treatment of melanoma or other cancers. Examples of oncolytic HSV include, but are not limited to talimogene laherparepvec (U.S. Pat. Nos. 7,223,593 and 7,537,924); OncoVEXGALV/CD (U.S. Pat. No. 7,981,669); OrienX010 (Lei et al. (2013), World J. Gastroenterol., 19:5138-5143); G207, 1716; NV1020; NV12023; NV1034 and NV1042 (Vargehes et al. (2002), Cancer Gene Ther., 9 (12): 967-978).

Also included are TIMPs. TIMPs are endogenous tissue inhibitors of metalloproteinases (TIMPs) and are important in many natural processes. TIMP-3 is expressed by various cells or and is present in the extracellular matrix; it inhibits all the major cartilage-degrading metalloproteases, and may play a role in role in many degradative diseases of connective tissue, including rheumatoid arthritis and osteoarthritis, as well as in cancer and cardiovascular conditions. The amino acid sequence of TIMP-3, and the nucleic acid sequence of a DNA that encodes TIMP-3, are disclosed in U.S. Pat. No. 6,562,596, issued May 13, 2003, the disclosure of which is incorporated by reference herein. Description of TIMP mutations can be found in U.S. Publication No. 2014/0274874 and PCT Publication No. WO 2014/152012.

Also included are antagonistic antibodies for human calcitonin gene-related peptide (CGRP) receptor and bispecific antibody molecule that target the CGRP receptor and other headache targets. Further information concerning these molecules can be found in PCT Application No. WO 2010/075238.

Additionally, bispecific T cell engager (BiTE®) antibodies, e.g. BLINCYTO® (blinatumomab), can be used in the device. Alternatively, included can be an APJ large molecule agonist e.g., apelin or analogues thereof in the device. Information relating to such molecules can be found in PCT Publication No. WO 2014/099984.

In certain embodiments, the medicament comprises a therapeutically effective amount of an anti-thymic stromal lymphopoietin (TSLP) or TSLP receptor antibody. Examples of anti-TSLP antibodies that may be used in such embodiments include, but are not limited to, those described in U.S. Pat. Nos. 7,982,016, and 8,232,372, and U.S. Publication No. 2009/0186022. Examples of anti-TSLP receptor antibodies include, but are not limited to, those described in U.S. Pat. No. 8,101,182. In particularly preferred embodiments, the medicament comprises a therapeutically effective amount of the anti-TSLP antibody designated as A5 within U.S. Pat. No. 7,982,016.

Although the drug delivery devices, methods, and components thereof, have been described in terms of exemplary embodiments, they are not limited thereto. The detailed description is to be construed as exemplary only and does not describe every possible embodiment of the invention because describing every possible embodiment would be impractical, if not impossible. Numerous alternative embodiments could be implemented, using either current technology or technology developed after the filing date of this patent that would still fall within the scope of the claims defining the invention. For example, components described herein with reference to certain kinds of drug delivery devices, such as on-body injector drug delivery devices or other kinds of drug delivery devices, can also be utilized in other kinds of drug delivery devices, such as autoinjector drug delivery devices.

Those skilled in the art will recognize that a wide variety of modifications, alterations, and combinations can be made with respect to the above described embodiments without departing from the scope of the invention, and that such modifications, alterations, and combinations are to be viewed as being within the ambit of the inventive concept.

The invention claimed is:

1. A drug delivery device, comprising: a syringe assembly including a needle; a handle adapted to house at least a portion of the syringe assembly, the handle including a first portion that is an upper surface at an end of the drug delivery device, a second portion including a lower surface, a tapered surface, and a window, the first portion being wider than the second portion, the needle of the syringe assembly adapted to extend from adjacent the second portion during an injection procedure, the window positioned between the first portion and the second portion and adapted to allow contents of the drug delivery device to be viewed; and a base positioned adjacent to the lower surface of the second portion of the handle during at least the injection procedure, the base being wider than the second portion of the handle and adapted to increase stability of the drug delivery device during the injection procedure, wherein the drug delivery device is arranged along a longitudinal axis, the upper surface including a topmost surface positioned within a plane that is perpendicular to the longitudinal axis and is topmost of the drug delivery device along the longitudinal axis during an injection procedure and a corner surface connected to the topmost surface and terminating at an exterior edge immediately upon bending to be perpendicular to the plane, and the tapered surface extends from the upper surface to the second portion, wherein the tapered surface tapers inwardly continuously from the exterior edge at the end of the drug delivery device to the lower surface of the second portion.

2. The drug delivery device of claim 1, wherein the base includes a flange that extends outwardly from the second portion of the handle.

3. The drug delivery device of claim 2, wherein the base includes a seal positioned between portions of the flange, the seal being at least one of pierceable by the needle of the syringe assembly during the injection procedure or removable prior to the injection procedure taking place.

4. The drug delivery device of claim 1, wherein the base includes a suction cup that faces away from the second portion of the handle.

5. The drug delivery device of claim 1, wherein the base includes a concave cross-section that faces away from the second portion of the handle.

6. The drug delivery device of claim 1, wherein the handle is removably coupled to the base via a snap-fit connection or a threaded connection.

7. The drug delivery device of claim 1, wherein the base includes a cradle comprising a collar and a flange, the collar defining a bore adapted to receive the second portion of the handle during the injection procedure.

8. The drug delivery device of claim 7, wherein the cradle comprises a seal that defines a portion of the bore.

9. The drug delivery device of claim 8, wherein the seal is at least one of pierceable by the needle of the syringe assembly during the injection procedure or removable prior to the injection procedure taking place.

10. The drug delivery device of claim 1, wherein the second portion of the handle comprises a needle guard.

* * * * *